(12) United States Patent  
Yamazaki et al.

(10) Patent No.: US 8,187,852 B2
(45) Date of Patent: May 29, 2012

(54) POROUS FILM (75) Inventors: Hidekazu Yamazaki, Minami-ashigara (JP); Tsukasa Ishihara, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 489 days.

(21) Appl. No.: 12/411,972

(22) Filed: Mar. 26, 2009

(65) Prior Publication Data

US 2009/0246865 A1 Oct. 1, 2009

(30) Foreign Application Priority Data

Mar. 28, 2008 (JP) ................. 2008-088794

(51) Int. Cl.
*C12N 11/08* (2006.01)
*C12N 5/00* (2006.01)
*C12M 3/00* (2006.01)

(52) U.S. Cl. ...... 435/180; 435/395; 435/397; 435/287.1

(58) Field of Classification Search .................. None
See application file for complete search history.

(56) References Cited

U.S. PATENT DOCUMENTS

| | | | | |
|---|---|---|---|---|
| 2,898,910 A | * | 8/1959 | Gross et al. | 602/59 |
| 4,704,198 A | * | 11/1987 | Ebersole et al. | 204/469 |
| 5,236,588 A | * | 8/1993 | Zhang et al. | 210/500.35 |
| D387,169 S | * | 12/1997 | Dunshee et al. | D24/189 |
| 2006/0281172 A1 | | 12/2006 | Kuwabara et al. | |
| 2007/0256941 A1 | * | 11/2007 | Prasad et al. | 205/775.5 |

FOREIGN PATENT DOCUMENTS

| | | |
|---|---|---|
| JP | 2001-157574 A | 6/2001 |
| JP | 2006-68080 A | 3/2006 |

* cited by examiner

*Primary Examiner* — Chris R Tate
*Assistant Examiner* — Douglas F White
(74) *Attorney, Agent, or Firm* — Sughrue Mion, PLLC (57) ABSTRACT

A porous film is used as a cell culture substrate that is a scaffold for a spheroid. The porous film has a plurality of pores whose diameters gradually increase in a direction A. The diameters of the pores gradually increase from a first area P1 to a third area P3 in this order. The first to the third areas P1 to P3 are located on the porous film along the direction A. The diameters and depths of the pores increase in proportion to the distance in the direction A.

3 Claims, 8 Drawing Sheets

POROUS FILM

FIELD OF THE INVENTION

The present invention relates to a porous film having a plurality of pores.

BACKGROUND OF THE INVENTION

In the fields of optics and electronics, higher integration density, information of higher density, and image information with higher definition are required increasingly. For this reason, films with finer structures are strongly desired in such fields. Examples of such films include a polymer film with a honeycomb structure, namely, a plurality of micropores at a μm level in a honeycomb arrangement. The film with a fine structure is also desired in the medical field. For example, a film that provides scaffolds for the cell culture is needed (see, for example, Japanese Patent Laid-Open Publication No. 2001-157574). Such film is more suitable for the cell culture than a smooth film by virtue of fine projections and depressions formed on the film. The fine projections and the depressions are formed substantially uniformly on the film.

However, there is an increasing need for films with non-uniform structures. In the field of regenerative medical research, a material for culturing cells that grow into a living organism needs to have a nonuniform structure because the living organism has a nonuniform structure. A porous material is suggested to be used as a material (hereinafter referred to as cell culture substrate) that provides scaffolds for the cell culture. Such porous material is produced from bioabsorbable polymer and formed with a plurality of pores whose porosity and pore size gradually change (see, for example, Japanese Patent Laid-Open Publication No. 2006-068080).

A vessel for the cell culture is suggested (see, for example, U.S. Patent Application Publication No. 2006/0281172 corresponding to Japanese Patent Laid-Open Publication No. 2006-325532). The cell culture vessel is provided with plural areas for culturing cells. Each area is formed with projections and depressions. Each projection is circular in cross section, and the diameters of the circular cross sections vary with the area.

To culture cells in the porous material, an optimum diameter and an optimum depth of the pores depend on types of cells to be cultured. A suitable diameter and a suitable depth of the pores, for supplying oxygen and nutrition to cells and for releasing carbon dioxide and waste from cells effectively and efficiently, vary among cells. For this reason, screening of the cell culture substrates to find suitable dimensions and suitable conditions for the cell culture shortens time for selecting the cell culture substrate and determining the cell culture conditions.

The material disclosed in the Japanese Patent Laid-Open Publication No. 2006-068080 has a mixed area where the cell culture area and an area not used for the cell culture coexist. In addition, the conditions of the material vary in each area of the material. Therefore, the material is not suitable for screening including reproducibility test. On the other hand, in the material disclosed in the U.S. Patent Application Publication No. 2006/0281172, the diameters of the projections vary from one cell culture area to another, but are substantially identical in each cell culture area. However, there may be cases where the area with the projections and depressions suitable for the cell culture may not be found. In other words, although the cells cannot be cultured effectively in any of the above cell culture areas, there is a possibility that such cells can be cultured using a different cell culture substrate having pores whose diameters are somewhere between the minimum diameter and the maximum diameter of the projections of the material disclosed in the U.S. Patent Application Publication No. 2006/0281172. Therefore, such material is not necessarily suitable for screening.

SUMMARY OF THE INVENTION

An object of the present invention is to provide a porous film used as a cell culture substrate and a screening material of cell culture.

In order to achieve the above objects and other objects, a porous film of the present invention is formed from polymer, and has a plurality of pores formed in a surface of the porous film. Diameters of the pores gradually increase as the pores become away from a predetermined point.

It is preferable that the diameter of each of the pores increases in proportion to a distance between the predetermined point and the pore. It is preferable that a depth of each of the pores increases in proportion to a distance between the predetermined point and the pore.

It is preferable that the diameter of each of the pores increases in proportion to a distance between the pore and a line including the predetermined point. It is preferable that the line is orthogonal to a direction in which the diameters of the pores gradually increase. It is preferable that the depth of each of the pores increases in proportion to a distance between the pore and a line including the predetermined point.

It is preferable that the pores are used as cell culture areas for culturing cells.

With the use of the porous film of the present invention, cells are effectively cultured. Therefore, the porous film is used as the cell culture substrate. The porous film can be used as a screening material. With the use of the porous film, screening for determining effective conditions for the cell culture is performed efficiently.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1A:
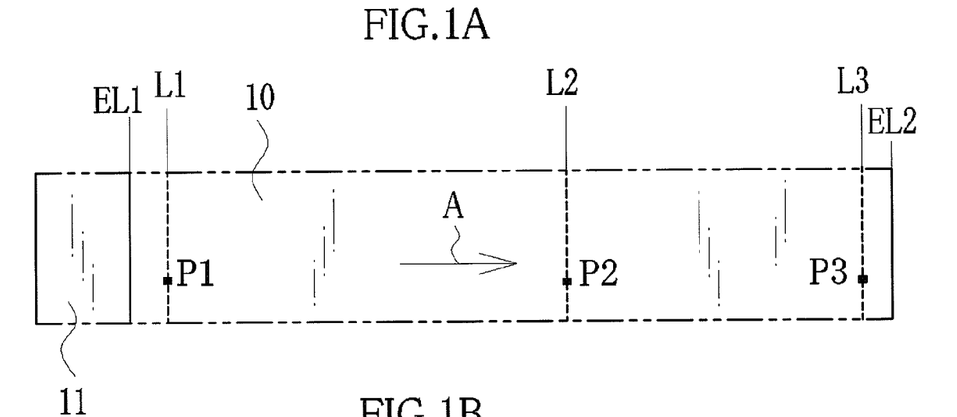
FIG. 1A is a plane view of a porous film of the present invention.

The present invention is not limited to a porous film 10 shown in FIG. 1A. In FIG. 1A, the porous film 10 is on a support 11. However, the support 11 is not necessarily used. Generally, the thickness of the porous film decreases as the size of the pores decreases. Handling of the porous film 10 becomes more difficult as the thickness thereof decreases. In view of handling, therefore, the porous film 10 with the support 11 may be sold as a product. The porous film 10 may be used without being separated from the support 11. Alternatively, the porous film 10 may be peeled from the support 11 and used.

A plurality of pores 12 are provided on one surface of the porous film 10. Each pore 12 is not a through hole that penetrates the porous film 10 in a thickness direction. The pores 12 are substantially uniform in shape, and are regularly arranged to like a honeycomb. A diameter D of the pore 12 is larger than a diameter AP of an aperture of the pore 12. Hereinafter, the diameter AP of the aperture may be referred to as aperture diameter AP. The diameter D is smaller than a distance L between centers of adjacent pores 12. The pores 12 are independent from each other and a path is not formed between the pores 12. However, the present invention includes both the porous films with independent pores such as the porous film 10 and the porous films of a honeycomb structure formed with paths connecting the pores.

The pores 12 are substantially uniform in shape, namely, all the pores 12 are similar to each other. The pores 12 as spaces for culturing cells are substantially identical in shape. In determining the cell culture substrate and conditions suitable for culturing cells, the shape variation of the pores 12 is an important factor that should be eliminated to perform a successful cell culture. Therefore, the porous film 10 is suitably used as a screening material for culturing cells.

Figure 2:
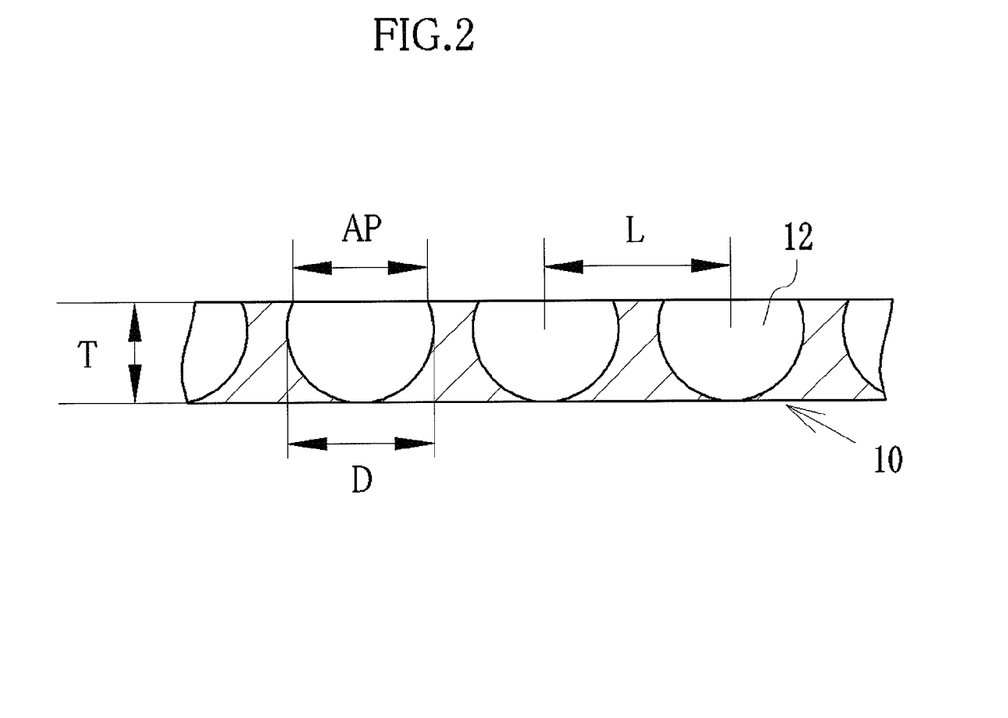
FIG. 2 is a cross-sectional view along a line II-II in FIG. 1C.

In a case that the pores 12 are independent from each other as shown in FIG. 2, cells can take in oxygen and nutrition, and release carbon dioxide and wastes effectively and uniformly in each pore 12. Therefore, such pores 12 are suitably used as a cell culture substrate or a screening material for culturing cells.

Figure 1B:
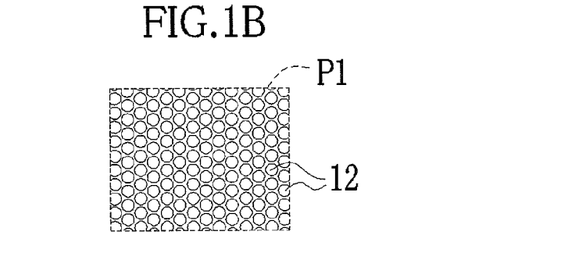
FIG. 1B is an enlarged view of a first area P1 shown in FIG. 1A.
Figure 1C:
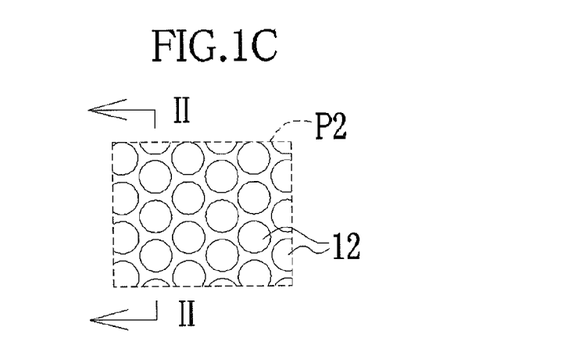
FIG. 1C is an enlarged view of a second area P2 shown in FIG. 1A.
Figure 1D:
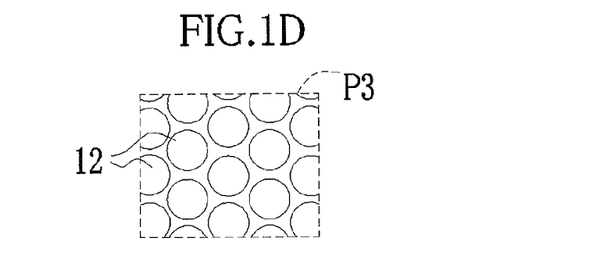
FIG. 1D is an enlarged view of a third area P3 shown in FIG. 1A.

The pores 12 are formed such that diameters D gradually increase from an end EL1 toward the other end EL2 of the porous film 10, namely, in a direction A shown by an arrow A in FIG. 1A. As shown in FIG. 1A, for example, three areas, a first area P1, a second area P2, and a third area P3 are selected on the porous film 10 in the direction A. As shown in FIGS. 1B, 1C, and 1D, the diameters D increase from the first area P1 to the third area P3 in this order. The first area P1 shown in FIG. 1B, the second area P2 shown in FIG. 1C, and the third area P3 shown in FIG. 1D are at the same magnification. The diameters D do not gradually increase or decrease in random directions, but gradually increase in the direction A. This regularity in the porous film 10 makes it easy to find a suitable area for the cell culture. The size of the pores 12 to be used as the cell culture substrate is easily determined. It should be noted that the apertures AP gradually increase in accordance with the increase of the diameters D in the direction A from the first area P1 to the third area P3 in this order. The number of the pores 12 per unit area gradually decreases in the direction A.

In a case that the diameter D increases in proportion to the distance between the end EL1 and the center of the pore 12, the diameter D in the third area P3 is obtained with a mathematical expression: (the diameter D in the second area P2)× D2/D1 in which D1 represents a distance between the first area P1 and the second area P2, and D2 represents a distance between the first area P1 and the third area P3.

Such regularity of the porous film 10, namely, the increase of the diameter D in proportion to the distance of the pore 12 in the direction A, makes it easy to select a suitable area for the cell culture. It becomes easy to determine the following: (1) a minimum diameter and a maximum diameter used for culturing predetermined cells (2) in a case that a nonuniform cell culture substrate is necessary, a suitable diameter difference between adjacent pores 12 in one direction and a suitable ratio between the diameters D of the adjacent pores 12. Hereinafter, adjacent two areas, each 1 mm×1 mm, on the same plane of the porous film 10 are selected in the direction A. An average value of the diameters D is calculated in each area. A difference between the two average values is referred to as the diameter difference.

It should be noted that the present invention is not limited to a case that the diameters D increase in proportion to the distance in the direction A. The present invention includes, for example, exponential or logarithmic increase of the diameters D.

The present invention includes a case that the pores 12 located on a given line orthogonal to the direction A are substantially identical in size. For example, there are lines L1, L2, and L3 all orthogonal to the direction A. The lines L1, L2, and L3 pass over the first area P1, the second area P2, and the third area P3, respectively. The pores 12 on the line L1 are substantially identical in size, diameter, and aperture diameter AP. The pores 12 on the line L2 are substantially identical in size, diameter, and aperture diameter AP. The pores 12 on the line L3 are substantially identical in size, diameter, and aperture diameter AP.

An average diameter DA of the pores 12 aligned on the first line L1, and an average diameter DS of the pores 12 in a given area A of 1 mm×1 mm is obtained. The area A is randomly selected on the line L1. The pores 12 are regarded as substantially identical in size when a coefficient of diameter variation obtained by 100×(DA−DS)/DS is at most 10%.

In a case that the diameters D are substantially identical in a direction orthogonal to the direction A and the diameters D change only in the direction A, plural unit areas with the identical structure are available. Such unit areas make it easy to perform screening or reproducibility tests of the cell culture. When the diameters D gradually but randomly increase, it is difficult to assume the relationship between the diameters D and the cell culture conditions. The porous film 10, however, has pores 12 whose diameters D regularly and gradually increase in one direction. As a result, the relationship between the diameters D and the cell culture conditions is assumed easily.

The thickness T of the film may be uniform or gradually increase in the direction A. In a case that the thickness T gradually increases in the direction A, the porous film 10 has the smallest thickness T at the end EL1, and the largest thickness T at the end EL2. The thickness T may increase in proportion to the distance of the pore 12 from the end EL1 in the direction A. In this case, the depth of the pore 12 may increase in proportion to the thickness T. Namely, the depth of the pore 12 increases in proportion to the distance of the pore 12 from the end EL1 in the direction A. Accordingly, an area suitable for culturing cells is more precisely determined not in two dimensions such as by the diameter D, but in three dimensions.

Figure 3:
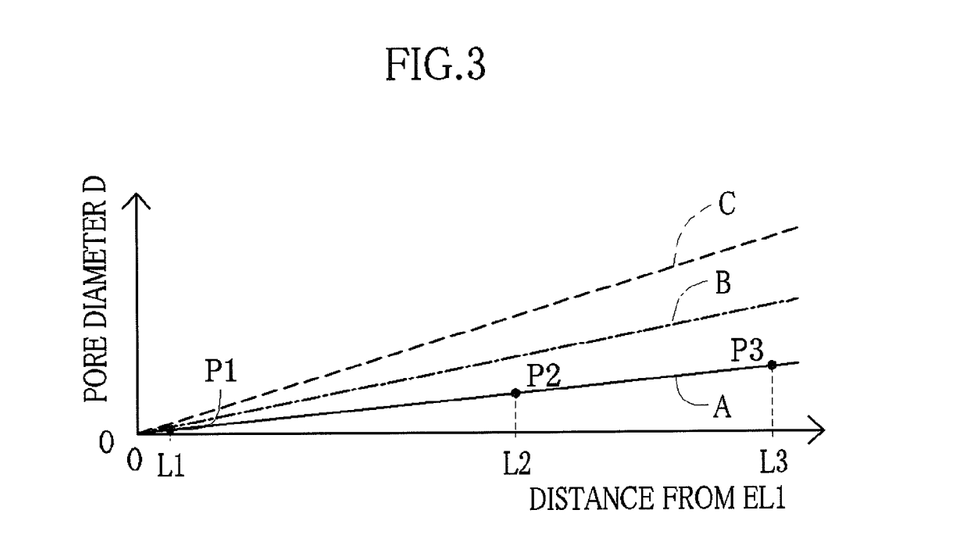
FIG. 3 is a graph showing a relationship between a diameter of a pore and a distance between one end of the porous film and the pore.

FIG. 3 shows an example of the present invention, but the present invention is not limited to the relationships shown in a graph of FIG. 3. In the graph, a vertical axis represents the diameter D, and the horizontal axis represents the distance from the end EL1 in the direction A. The diameter D increases in proportion to the distance in the direction A. The diameter D increases linearly. Here, a diameter difference between the diameters D in the direction A is at most 4 μm. Examples of the diameter difference may be in a range from 20 nm to 4 μm, from 100 nm to 2 μm, or the like. The diameter difference is determined by the purpose. In the porous film, the diameter difference is within an extremely small range so that the graph of the diameter D and the distance from the end EL1 show the linear increase. For example, a line A, alternate short and long dashed lines B, and short dashed lines C represent the porous film 10 with the diameter difference of 0.05 μm, 0.08 μm, and 0.1 μm, respectively. The diameter difference is a difference between the diameters D of the adjacent pores 12. The slopes of the line A, the alternate short and long dashed lines B, and short dashed lines C increase in this order. It should be noted that the origin point is excluded. The present invention includes various porous films 10 with different diameter differences in the direction A.

A suitable diameter for culturing cells may not be determined when the diameters D of the pores 12 increase stepwise in the cell culture substrate. For example, cells supposed to be cultured in the cell culture substrate with the pores 12 in a range from 3.3 μm to 3.5 μm in diameter cannot be cultured, or a fact that the suitable diameter for each cell is in a range from 3.3 μm to 3.5 μm cannot be identified, when the cell culture substrate used only has the pores 3.0 μm and 4.0 μm in diameter. In the present invention, however, the diameters D of the porous film 10 gradually and linearly increase. As a result, a suitable or an available area for culturing the cells can be identified even in the above case.

In the porous film 10, the minimum diameter is 10 nm, and the maximum diameter is 200 μm. The diameter D linearly increases in the direction A. For example, when there is the diameter difference of 20 nm, the minimum diameter is in a range from 10 nm to 1 μm, and the maximum diameter is in a range from 500 nm to 10 μm. When there is the diameter difference of 4 μm, the minimum diameter is in a range from 1 μm to 10 μm, and the maximum diameter is in a range from 20 μm to 200 μm. The minimum diameter is the diameter D of the pore 12 closest to the end EL1. The maximum diameter D of the pore 12 is the diameter D of the pore 12 closest to the end EL2.

The above-configured porous film 10 is suitable for the cell culture substrate of a spheroid (three-dimensional cell culture). The porous film 10 is also suitable for screening of the cell culture substrates for use in culturing various cells. In particular, the porous film 10 is preferable for the cell culture substrates and screening material for nerve cells and hepatic cells. This is because, in culturing nerve cells, conditions in forming a spheroid vary depending on thicknesses, lengths, extending directions of dendrites projecting from a cell body, a length and an extending direction of an axon, thicknesses, lengths, and extending directions of axon collaterals, and lengths of axon terminals. And in culturing hepatic cells, conditions in forming a spheroid vary depending on albumin synthetic capability.

The porous film 10 is formed from organic polymer. Therefore, the porous film 10 is excellent in flexibility, and can be used along a curved surface. A desired area of the porous film 10 can be cut into a desired shape for use.

Examples of the method for producing the porous film 10 include a condensation method, a well-known nanoimprint method, a lithography method, and an emulsion method. In the emulsion method, a liquid emulsion containing polymer is cast onto a support, and dried. Thereby, water contained in a water phase formed discontinuously within an oil phase (polymer layer) is evaporated from the oil phase. Micropores are formed by the evaporation of water. Examples of the nanoimprint method are disclosed in Japanese Patent Laid-Open Publication No. 2004-566288. Examples of the lithography method are disclosed in Japanese Patent Laid-Open Publication No. 2005-061961. Examples of the emulsion method are disclosed in Japanese Patent Laid-Open Publication No. 2003-166982.

In the condensation method, a casting solution is prepared by dissolving hydrophobic polymer in a solvent. A casting film is formed by casting the casting solution onto a support. Water droplets are generated on the casting film by condensation. The solvents and the water droplets are evaporated. Thus, the porous film 10 with a plurality of the pores 12 is formed. The condensation method is more preferable than the above three other methods in view of smaller diameter difference, production efficiency, and production cost in forming the pores 12 whose diameters D increase in the direction A. Hereinafter, the condensation method for producing the porous film 10 is described.

In the following condensation method, the porous film 10 whose thickness T increases in proportion to the distance in the direction A is produced.

[Raw Material]

Hydrophobic polymer is preferred as the polymer. An amphipathic compound may be used in addition to the hydrophobic polymer. The amphipathic compound is both hydrophilic and lipophilic. More specifically, the amphipathic compound has a hydrophilic group and a hydrophobic group. The amphipathic compound makes it easier to generate water droplets on an exposed surface of a casting film.

The hydrophobic polymer used in combination with the amphipathic compound is preferred to be soluble in a water-insoluble or hydrophobic solvent. For example, poly-ϵ-caprolactone, poly-3-hydroxybutyrate, agarose, and poly-2-hydroxyethylacrylate, and polysulfone are preferably used. Especially, poly-ϵ-caprolactone is preferable in a case that biodegradability is necessary or in view of availability and low cost.

Other examples of the hydrophobic polymer used in combination with the amphipathic compound includes vinyl-type polymer (for example, polyethylene, polypropylene, polystyrene, polyacrylate, polymethacrylate, polyacrylamide, polymethacrylamide, polyvinyl chloride, polyvinylidene chloride, polyvinylidene fluoride, polyhexafluoropropene, polyvinyl ethers, polyvinyl carbazole, polyvinyl acetate, polytetrafluoroethylene and the like), polyesters (for example, polyethylene terephthalate, polyethylene naphthalate, polyethylene succinate, polybutylene succinate, polylactate and the like), polylactones (for example, polycaprolactone and the like), polyamides and polyimides (for example, nylon, polyamic acid and the like), polyurethane, polyurea, polycarbonate, polyaromatics, polysulfone, polyethersulfone, polysiloxane derivatives and the like. These may be used in the form of homopolymer, copolymer, a polymer blend, or a polymer alloy in view of solubility, optical physical properties, electric physical properties, film strength, elasticity and the like.

Examples of the amphipathic compound used in combination with the hydrophobic polymer include monomers such as commercially available surfactants, oligomers such as dimers and trimers, and polymers. To use the amphipathic compound in combination with the hydrophobic polymer, a weight ratio of the amphipathic compound to the hydrophobic polymer is preferred to be in a range from 0.1% to 20%.

The solvent used for the preparation of the casting solution is not particularly limited as long as hydrophobic polymer is dissolved therein. Examples of the solvents include chloroform, dichloromethane, tetrachlomethane, cyclohexane, and methyl acetate.

The generation speed of the water droplets and the depths of the water droplets inside the casting film 20 are controlled by combining two or more kinds of compounds and changing the proportions thereof as necessary.

It is preferred that the casting solution contains at least 0.02 pts. wt. and at most 20 pts. wt. of the hydrophobic polymer, and 100 pts. wt. of organic solvent. It is preferred to adjust fluidity, or easiness to flow, of the casting solution within this range of the weight concentration.

As the viscosity of the casting solution increases, it becomes more difficult to arrange the water droplets generated by condensation, and fluidity of the casting solution decreases. On the other hand, as the viscosity of the casting solution decreases, the water droplets are more likely to join together so that the diameters D become nonuniform. To prevent the above problems, the viscosity is controlled within a range from 0.1 mPa·s to 50 mPa·s. It is preferred to adjust the fluidity of the casting solution while the viscosity thereof is kept within the above range. The thickness T, the diameter D, and the diameter difference are adjusted by adjusting the fluidity of the casting solution.

Figure 4A:
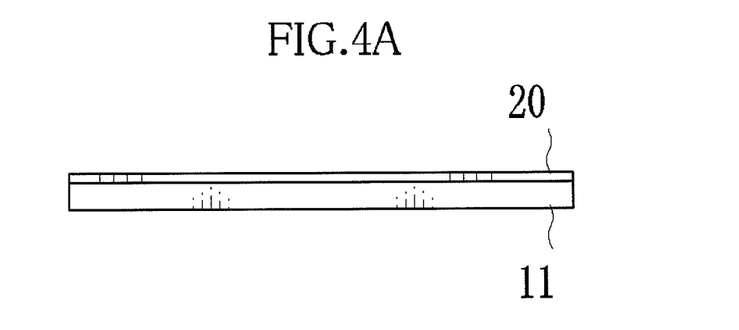
FIGS. 4A, 4B, and 4C are explanatory views of a producing method of a porous film.

The casting solution is cast on the support 11. As the casting method, there are a method to cast the casting solution on the moving support 11, and a method to cast and spread the casting solution on the support 11. Either method can be used. Thereby, as shown in FIG. 4A, a casting film 20 is formed on the support 11. During the casting process, the support 11 and the casting solution are preferred to be in a dry atmosphere.

Figure 4B:
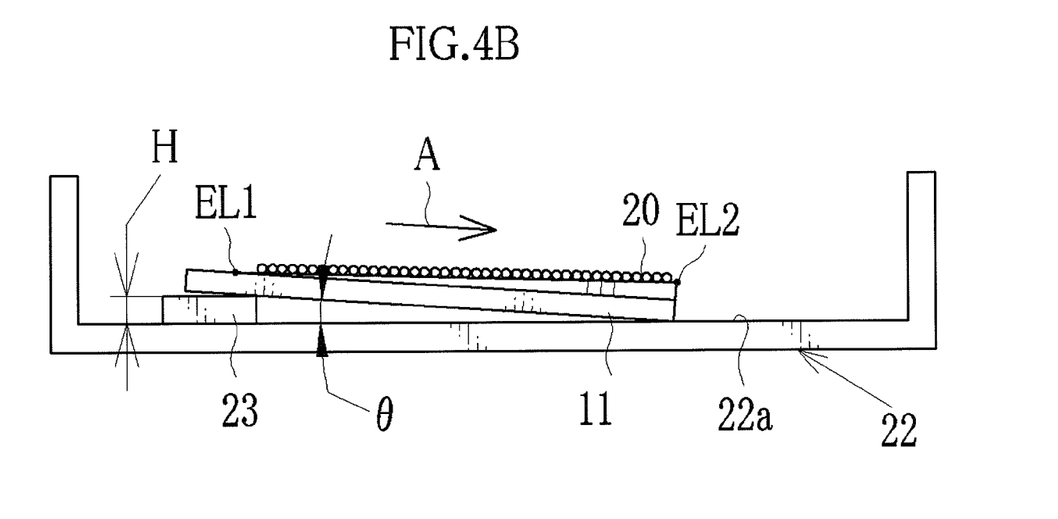

The support 11 is placed in a container 22. An inclination-angle keeper 23 is placed on a bottom 22a of the container 22. The inclination-angle keeper 23 holds the support 11 in an inclined state. As shown in FIG. 4B, the support 11 is placed inclined on the bottom 22a while one end of the support 11 is held by the inclination-angle keeper 23. The thickness of the fluid casting film 20 increases along the inclined support 11. As described above, the casting solution can be cast onto the inclined support 11. In FIG. 4B, the thickness of the casting film increases along the direction A shown by the arrow A as with the FIG. 1A. The casting film 20 flows along the direction A when the support 11 is inclined. Thereby, the thickness of the casting film 20 increases along the direction A. The thickness of the casting film 20 increases in proportion to the distance in the direction A.

A difference and a ratio between a minimum value and a maximum value of the diameters D increase as a difference between the thicknesses of the casting film 20 at the end EL1 and the end EL2 increase. To increase the difference between the thicknesses of the casting film 20 at the end EL1 and the end EL2, the viscosity of the casting solution is increased and/or an inclination angle θ of the support 11 is increased by making a height H of the inclination-angle keeper 23 higher.

Namely, a difference in the diameters D between adjacent pores 12 in the direction A, a minimum diameter, a maximum diameter, a difference between the minimum diameter and the maximum diameter are controlled by adjusting at least one of the inclination angle θ of the support 11 and the viscosity of the casting solution. The porous films, represented by lines (A) to (C) of a graph showing the relationship between the diameter D and the distance of the pore 12 from the end EL1 in FIG. 3, or other porous films represented by lines with slopes different from those of the lines (A) to (C) can be produced by adjusting one of the inclination angle θ and the viscosity of the casting solution.

As described above, the maximum diameter D increases as the inclination angle θ and the viscosity of the casting solution increase. Such increases are due to a difference in drying speed between a point where the thickness T of the casting film 20 is small and a point where the thickness T is large. The difference in the drying speed increases as the inclination angle θ and the viscosity of the casting solution increase. The viscosity of the casting solution is increased by increasing the concentration of the polymer in the casting solution and/or using polymer with higher molecular weight.

The depth of the pore 12 is controlled by adjusting at least one of the inclination angle θ and the viscosity of the casting solution. Namely, a difference in the depth between the adjacent pores 12 in the direction A, a difference in the depth between the pore 12 closest to the end EL1 and the pore 12 closest to the end EL2 are controlled by adjusting the inclination angle θ and the viscosity of the casting solution. For example, in order to increase the difference in the depth between the pores 12, the inclination angle θ and the viscosity of the casting solution are increased. Thereby, the difference in the drying speed between a point where the thickness T is small and a point where the thickness T is large increases compared to a case where the inclination angle θ is small and the viscosity of the casting solution is low.

Water droplets (hereinafter may referred to as droplets) 25 are generated on the casting film 20 due to condensation. When generated, each droplet 25 is extremely small and cannot be visually identified. The size of each droplet is in a range from several nanometer to several tens nanometer. In FIG. 4B, the size of the droplets is exaggerated for the sake of convenience. In this condensation process (droplet generating process), humidified air (moist air) is contacted with the casting film 20. A duct (not shown) is disposed above the container 22. A blower (not shown) is connected to the duct. The blower feeds temperature-and-humidity-controlled air to the duct, and controls ON-OFF of the duct, the volume, and the velocity of air supplied from the duct. Start timing of the condensation and the size of the droplets 25 are controlled by air supplied from the duct. The temperature inside the container 22 may be lowered so as to lower the temperature of the casting film 20 before the casting film 20 comes in contact with the moist air. As a result, water contained in the moist air is condensed on the casting film 20 more easily.

In the droplet generating process, a value ΔT (unit: ° C.) is obtained by subtracting TS from TD (ΔT=TD−TS) in which TD represents a dew point of air from the duct, and TS represents a temperature of an exposed surface of the casting film 20. At least one of the temperature TS and the dew point TD is controlled to make ΔT satisfy the following condition (1).

$$0° C. < \Delta T \leq 30° C. \tag{1}$$

The temperature TS is measured using a non-contact thermometer such as a commercially available infrared thermometer disposed close to the casting film 20. When ΔT is 0° C. or less, it is difficult to generate the droplets 25. On the other hand, when ΔT is more than 30° C., the droplets 25 may be generated abruptly, which makes the size of the droplets 25 uneven at the start of generation of the droplets 25.

The droplets 25 gradually grow after being generated. It is preferred to start the condensation after the grade of the thickness T of the casting film 20 is formed. However, condensation may be started depending on the timing of generating the droplets 25 and the growing speed of the droplets 25.

The droplets 25 get into the casting film 20 as they grow. The casting film 20 is dried and hardened more quickly, namely, loses fluidity as the thickness thereof decreases. This blocks the droplets 25 from growing. The drying speed of the casting film 20 becomes slower as the thickness of the casting film 20 increases. As a result, the time for the droplets 25 to grow inside the casting film 20 is extended. Thus, the thickness T of the casting film 20 is increased in the direction A so as to extend the time needed for drying the casting film 20. Accordingly, the sizes of the droplets 25 gradually increase in the direction A. The support 11 is kept inclined during this droplet growing process.

In the droplet growing process, it is preferable to control at least one of the temperature TS and the dew point TD to make ΔT (unit: ° C.) satisfy the following condition (2).

$$0° C. < \Delta T \leq 20° C. \quad (2)$$

The temperature TS is controlled by a thermostat plate (not shown), for example. The container 22 is placed on the thermostat plate, and the thermostat plate controls the temperature of the container 22 via the bottom 22a of the container 22. In the droplet growing process, it is preferable to supply the moist air from the duct. The dew point TD is controlled by adjusting the temperature, the humidity, the volume, and the velocity of the moist air supplied from the duct.

During and/or after the droplet growing process, the solvent contained in the casting film 20 is evaporated. This solvent evaporation process is performed by contacting dry air with the casting film 20. The dry air may be supplied using the duct used for supplying the moist air in the condensation process. Alternatively, an independent duct may be provided for supplying the dry air. Timing to stop the growth of the droplets 25, and the evaporation speed of the solvent are controlled by the dry air supplied from the duct. The maximum diameter becomes smaller as the evaporation speed of the solvent increases. Thus, the maximum diameter can be controlled by adjusting the evaporation speed of the solvent.

It is preferable to perform the solvent evaporation process while the support 11 is kept in the inclined state. However, it is not necessary to keep the support 11 inclined when the droplets 25 closest to the end EL2 stops to grow inside the casting film 20, even if the solvent evaporation is not ended, because the casting film 20 is hardened. The support 11 should be kept inclined until the solvent evaporates to an extent that the casting film 20 loses fluidity.

When the droplets 25 achieves desired size and state, the droplets 25 inside the casting film 20 are evaporated to produce water vapor 27. When the solvent is remaining in the casting film 20, the droplets 25 are evaporated after the remaining solvent is evaporated as much as possible. In this droplet evaporation process, as with the solvent evaporation process, dry air is supplied from the duct onto the casting film 20. The duct is provided above the container 22. The evaporation speeds of the droplets 25 and the remaining solvent in the casting film 20 are controlled by adjusting the temperature, the volume, and the velocity of the dry air supplied from the duct.

In the droplet evaporation process, it is not necessary to keep the support 11 inclined. However, the support 11 may be kept in the inclined state. The droplets 25 may be evaporated from the casting film 20 while the support is placed in a horizontal position or kept inclined on the container 22.

Thus, the porous film 10 is produced on the support 11. The diameter D of the pore 12 on the produced porous film 10 increases in proportion to the distance of the pore 12 in the direction A. By this method, the thickness T of the porous film 10 increases in proportion to the distance of the pore 12 in the direction A. The support 11 may be peeled off from the porous film 10 during or after the production of the porous film 10 when the support 11 is unnecessary.

Figure 4C:
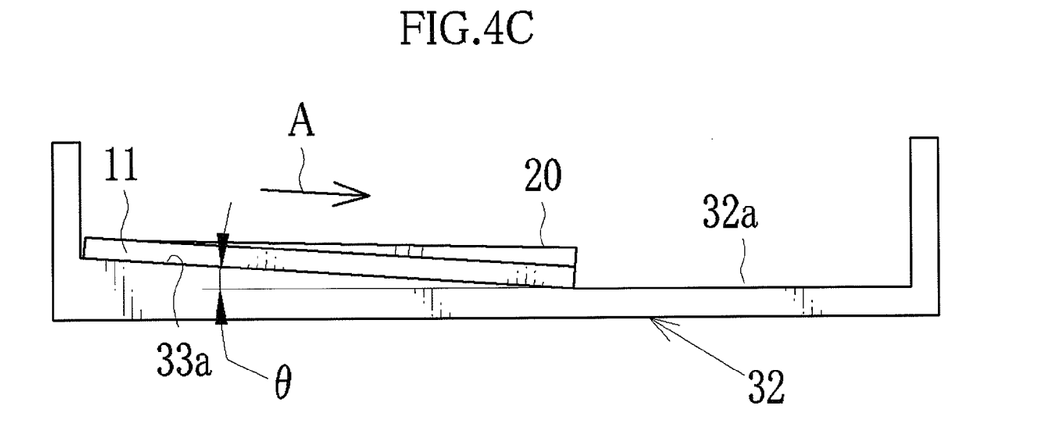

Instead of using the container 22 and the inclination-angle keeper 23 shown in FIG. 4B, a container 32 shown in FIG. 4C may be used. The container 32 is provided with an inclined portion 32a to hold the entire undersurface of the support 11. The container 32 has the inclined portion 32a and a horizontal portion 32b. The inclined portion 32a descends to the horizontal portion 32b at a lower end. When the support 11 is placed in the container 32 in an inclined state, the lower end of the support 11 is supported by the horizontal portion 32b. When the casting solution for forming the casting film 20 flows off the support 11, such casting solution is accumulated in the horizontal portion 32b. When using the container 32, the difference in the diameters D between adjacent pores 12 in the direction A, the minimum diameter, the maximum diameter, the difference between the minimum diameter and the maximum diameter are controlled by adjusting at least one of the inclination angle θ of the inclined portion 32a and the viscosity of the casting solution.

It is also possible to provide at least three chambers, a first chamber, a second chamber, and a third chamber, in this order from the upstream of a path of a long belt. The support 11 is conveyed by the belt through the first to the third chambers to produce the porous film 10. The first chamber is provided with a duct that supplies dry air. The second chamber is provided with a duct that supplies moist air. The third chamber is provided with a duct that supplies dry air. A ventilation duct may be provided in each chamber to circulate air in each chamber.

In the first chamber, the casting solution is cast onto a support on the belt to form the casting film. During the conveyance of the support 11 from the first chamber to the inside of the second chamber, water vapor is condensed on the casting film and thus droplets are generated. When the droplets grow to desired size and state, the support 11 is conveyed to the third chamber. In the third chamber, the solvent and the droplets are evaporated.

A support roller may be disposed along the path of the belt. A circumferential surface of the support roller supports the belt from the undersurface of the belt. The support roller is driven by a drive roller that rotates in a circumferential direction, for example. The support roller is inclined such that a longitudinal direction thereof intersects with the horizontal plane. That means an end of the support roller is higher than the other end thereof in the width direction. Thus, the support 11 is conveyed by the support roller in the inclined state. By this method, the porous film is produced with the diameters D of the pores gradually increasing in the width direction of the belt. It should be noted that a long porous film can be formed by using the moving belt as the support onto which the casting solution is cast.

Figure 5A:
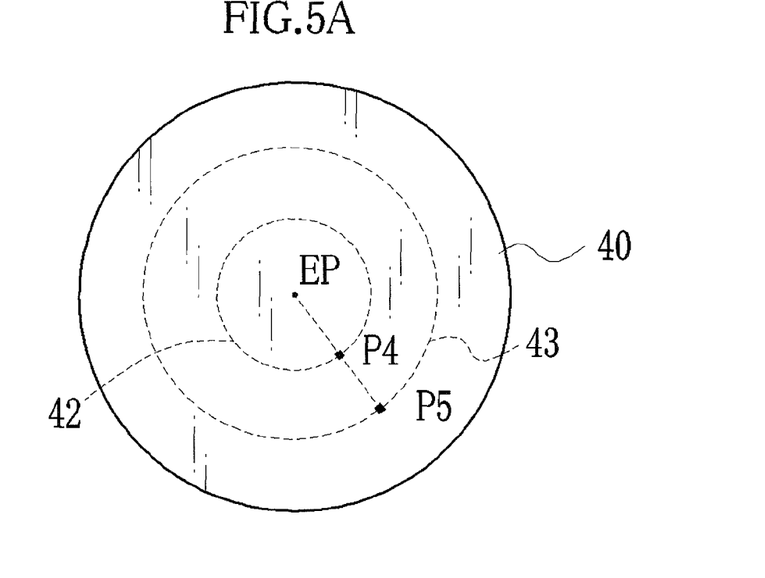
FIG. 5A is a plane view of a porous film of another embodiment.
Figure 5B:
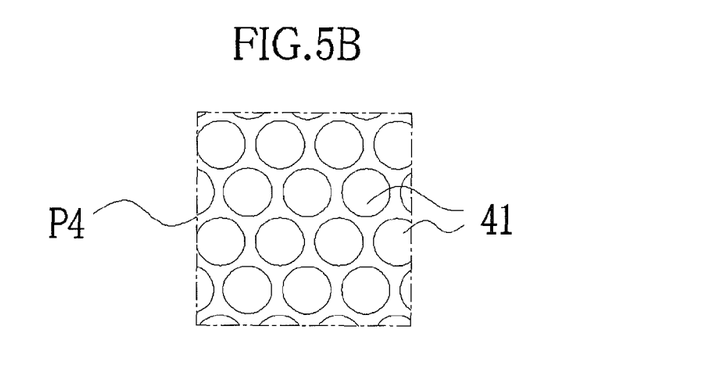
FIG. 5B is an enlarged view of a fourth area P4 shown in FIG. 5A.
Figure 5C:
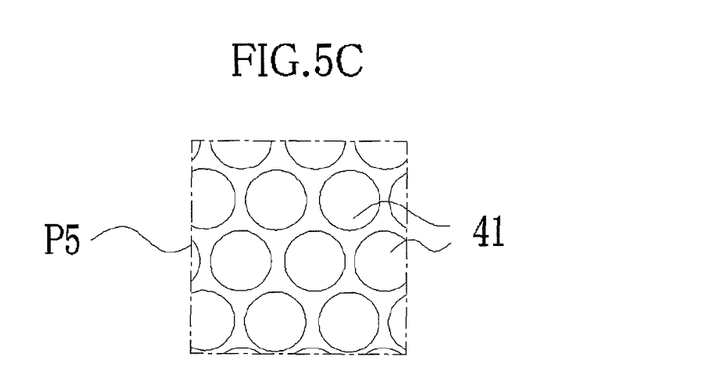
FIG. 5C is an enlarged view of a fifth area P5 shown in FIG. 5A.

In a second embodiment, as shown in FIG. 5A, a porous film 40 is formed with a plurality of pores 41. The diameter of the pores 41 gradually and concentrically increase from a point EP. A first circle 42 and a second circle 43 are concentric circles around the point EP. It should be noted that the first and second circles 42 and 43 are imaginary lines and indicated in FIG. 5A for the sake of convenience in description. In FIG. 5A, the first and second circles 42 and 43 are indicated by dashed lines. A fourth area P4 is located on the first circle 42. A fifth area P5 is located on the second circle 43. The point EP, the fourth area P4, and the fifth area P5 are aligned along a straight line in this order. The fourth area P4 shown in FIG. 5B and the fifth area P5 shown in FIG. 5C are magnified by the same scale from those shown in FIG. 5A. The diameter of the pore 41 gradually increases as a distance between the point EP and the pore 41 increases. In other words, the pores 41 in the fifth area P5 are larger than the pores 41 in the fourth area P4 in diameter. The pores 41 located at the same distance from the point EP have the same diameter. Namely, the pores 41 located on the first circle 42 have the same diameter. The pores 41 located on the second circle 43 have the same diameter. The distance and the diameter of the pore 41 satisfy the following: (a distance between the point EP and the fourth area P4): (a distance between the point EP and the fifth area P5)=(a diameter of the pore 41 at the fourth area P4): (a diameter of the pore 41 at the fifth area P5). In this embodiment, the thickness of the porous film 40 increases outward from the point EP gradually and concentrically.

Figure 6A:
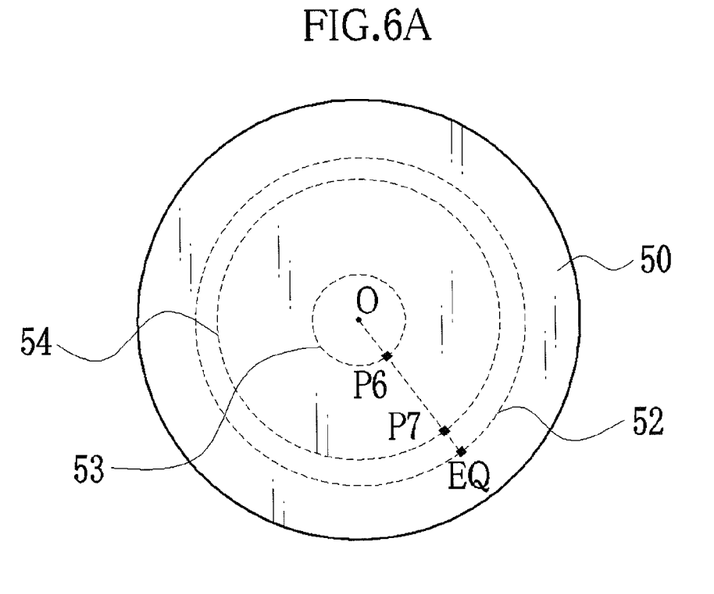
FIG. 6A is a plane view of a porous film of another embodiment.
Figure 6B:
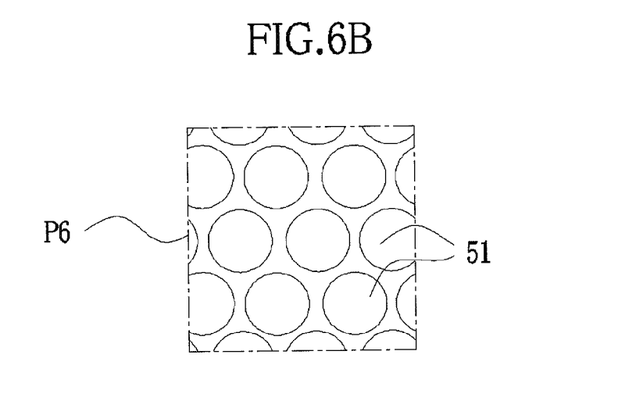
FIG. 6B is an enlarged view of a sixth area P6 shown in FIG. 6A.
Figure 6C:
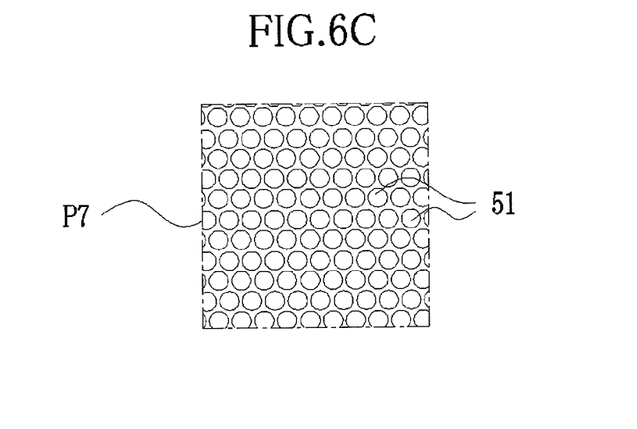
FIG. 6C is an enlarged view of a seventh area P7 shown in FIG. 6A.

In a third embodiment, as shown in FIG. 6A, a porous film 50 is formed with a plurality of pores 51. The diameters of the pores 51 gradually and concentrically decrease from a point 0. A first circle 52, a second circle 53, and a third circle 54 are concentric circles around the point O. It should be noted that the first, second, and third circles 52, 53, and 54 are imaginary lines and indicated in FIG. 6A for the sake of convenience in description. In FIG. 6A, the first, second, and third circles 52, 53, and 54 are indicated by dashed lines. A point EQ is located on the first circle 52. A sixth area P6 is located on the second circle 53. A seventh area P7 is located on the third circle 54. The point EQ, the seventh area P7, the sixth area P6, and the point 0 are aligned along a straight line in this order. The sixth area P6 shown in FIG. 6B and the seventh area P7 shown in FIG. 6C are magnified by the same scale from those shown in FIG. 6A. The diameter of the pore 51 gradually increases as a distance between the point EQ and the pore 51 increases. In other words, the pores 51 in the sixth area P6 are larger than the pores 51 in the seventh area P7 in diameter. The pores 51 located at the same distance from the point O have the same diameter. Namely, the pores 51 located on the first circle 52 have the same diameter. The pores 51 located on the second circle 53 have the same diameter. The pores 51 on the third circle 54 have the same diameter. The distance and the diameter of the pore 51 satisfy the following: (a distance between the point EQ and the seventh area P7): (a distance between the point EQ and the sixth area P6)=(a diameter of the pore 51 at the seventh area P7): (a diameter of the pore 51 at the sixth area P6). In this embodiment, the thickness of the porous film 40 decreases outward from the point O gradually and concentrically.

The porous films 40 and 50 are produced by forming casting films that concentrically change their thickness. To form such casting films, various known spin coating methods can be used, for example. In the spin coating method, a casting solution is cast onto a support and then the support is spun to spread the casting solution on the support, thereby forming desired thickness gradation in the casting film. The casting film is subject to the droplets generating process, the droplets growing process, and the solvent evaporation process. Thus the spin coating method is capable of forming a film in which diameters of the pores gradually increase outward in all directions from one point. As described above, the diameters of the pores formed in the film gradually increase or decrease, and the pores can be arranged with various diameter patterns in accordance with the thickness of the film so as to efficiently perform screening for determining effective conditions for the cell culture.

Figure 7A:
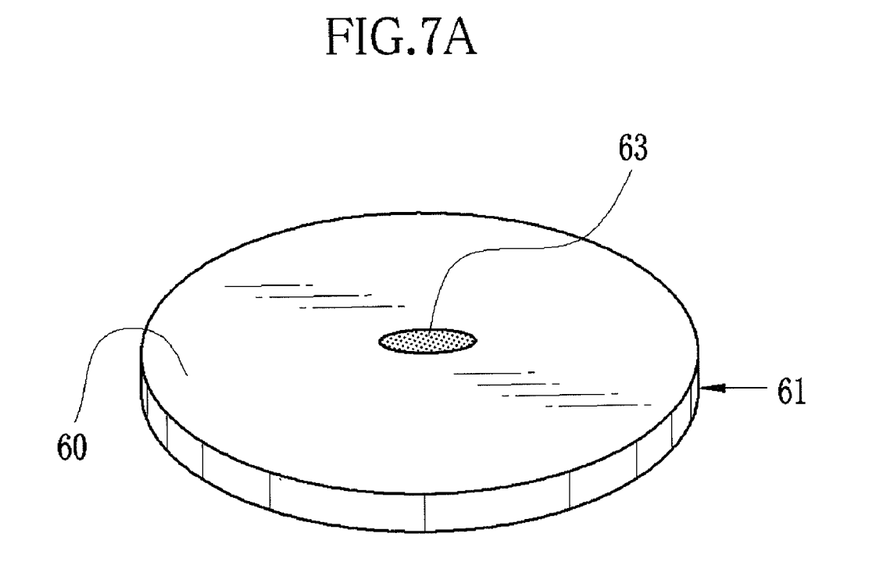
FIG. 7A is a perspective view of a support and FIG. 7B is a cross-sectional view of the support and a casting film formed on the support.
Figure 7B:
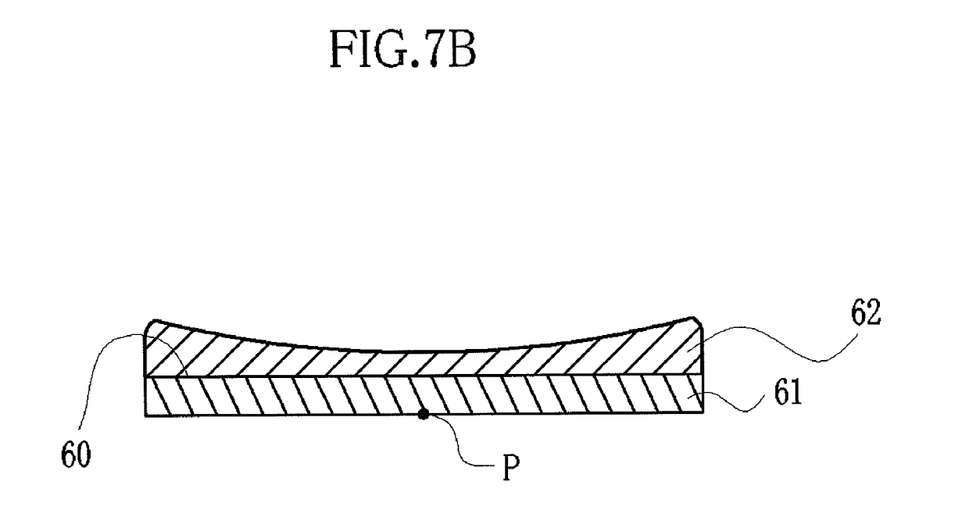

A method for producing the porous films 40 and 50 are described more specifically. To produce the porous film 40, for example, a support 61 with a horizontal and flat surface 60 is used as shown in FIGS. 7A and 7B. The support 61 shown in FIGS. 7A and 7B is disc-shaped. However, the shape of the support is not limited to it. A known spin coater (not shown) is used for producing a casting film 62. The spin coater has a rotation supporter and a controller (both not shown). The rotation supporter rotates the support 61 around a center P of the support 61 in a circumferential direction. The controller turns the rotation supporter on or off for rotating the support 61, and controls a rotation direction and a rotation speed. The support 61 is set in the rotation supporter and rotated by the rotation supporter at a predetermined rotation speed. The support 61 may be rotated while the surface 60 is kept horizontal. Alternatively, the support 61 may be tilted and rotated.

A casting solution 63 is applied to the surface 60 of the rotating support 61 to form the casting film 62. The thickness of the casting film 62 is adjusted by centrifugal force generated during the rotation of the support 61. The rotation speed of the support 61 is adjusted such that the thickness of the casting film 62 gradually increases outward from the center P as shown in FIG. 7B.

Figure 8A:
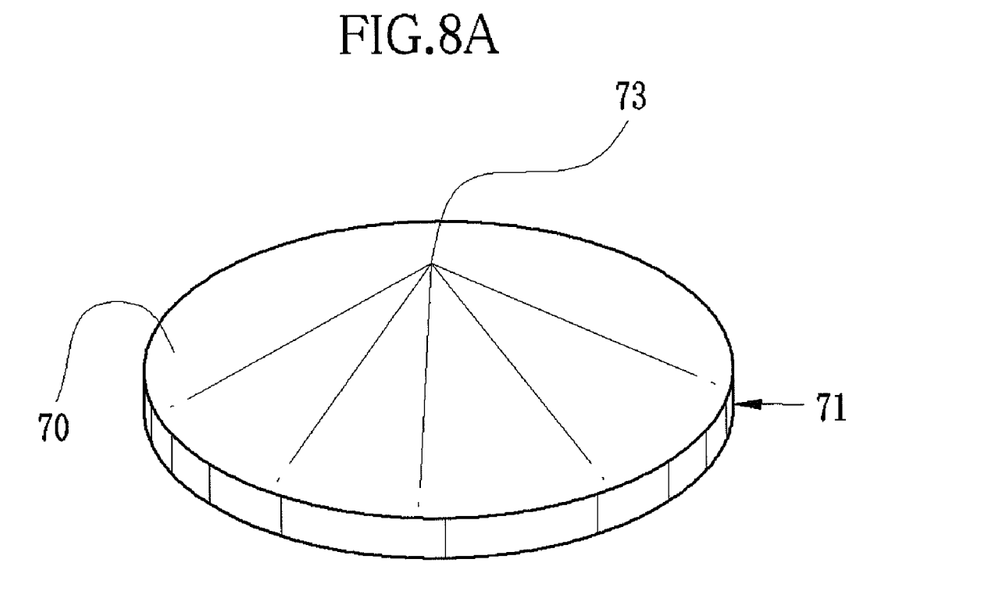
FIG. 8A is a perspective view of a support of a different shape and FIG. 8B is a cross-sectional view of the support and a casting film formed on the support.
Figure 8B:
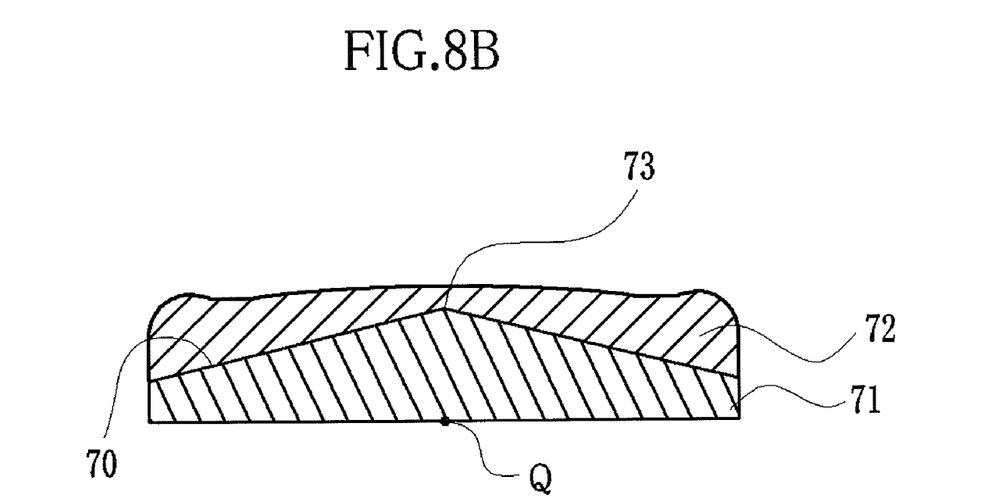

The casting film whose thickness gradually increases outward from its center can be formed using a support of a different type from the above. For example, a support 71 with a conical-shaped surface 70 may be used as shown in FIGS. 8A and 8B. The support 71 has a circular surface 70 with its height decreasing outward from a center Q. The surface 70 may be substantially conical, and a top 73 thereof may be round. The support 71 is rotated around the center Q and the top 73. The casting solution 63 is applied to the surface 70 of the rotating support 71, and rotation conditions are adjusted. Thus, the casting film 72 is formed. Alternatively, the casting solution 63 is applied to the support 71 in a still state or with the rotation supporter turned off. This method is also capable of forming the above described casting film whose thickness gradually increases outward. Instead of using the support 61 or 71, a support (not shown) having a round shape or a so-called domical shape may be used.

With the use of the support 61 with the horizontal and flat surface 60 as shown in FIGS. 7A and 7B, a casting film for producing the porous film 50 (see FIG. 6) is formed. In this case, the casting solution is applied to the surface 60 of the support, and rotation conditions of the support 61 is controlled to form a casting film 80 whose thickness gradually decreases outward from the center P as shown in FIG.9.

Figure 9:
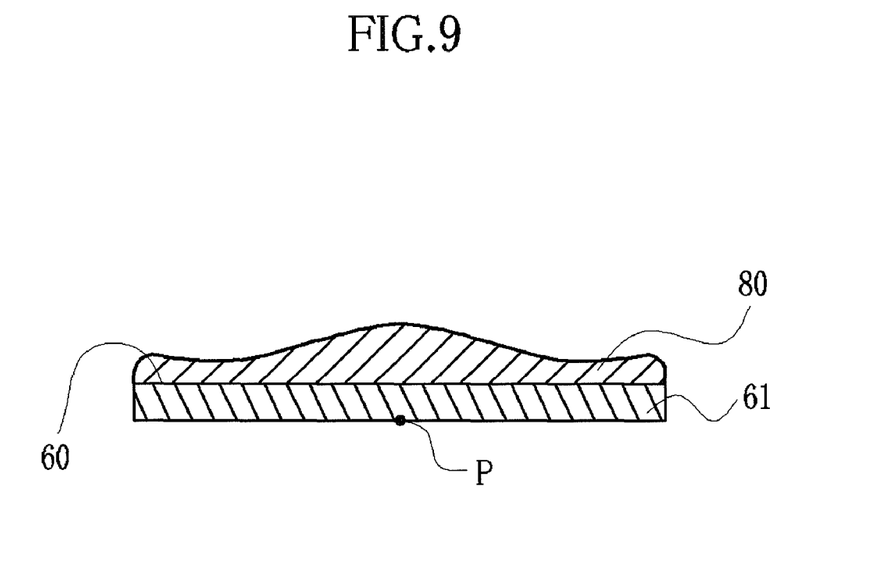
FIG. 9 is a cross-sectional view of the support and a casting film formed on the support.

Circumferential portions of the casting films 62, 72, and 80 formed by the above methods may be slightly protruded as shown in FIGS. 7B, 8B, and 9. In those cases, the pores are formed in an area excluding the protruded portion in each of the casting films 62, 72, and 80.

Figure 10:
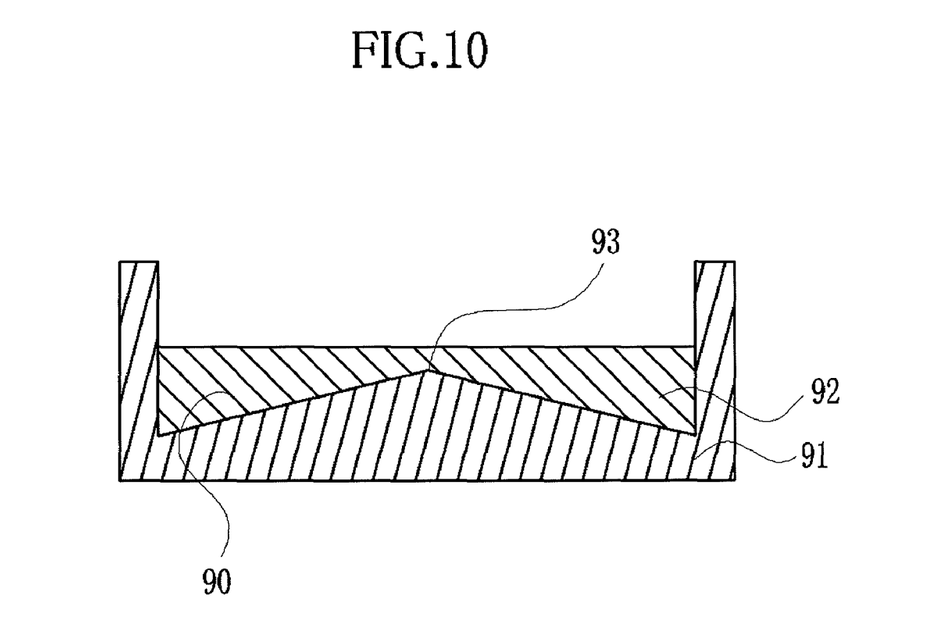
FIG. 10 is a cross-sectional view of a petri-dish-like vessel and a casting film formed in the vessel.

A casting film whose thickness gradually increases outward from the center can be formed by other methods. For example, as shown in FIG. 10, a casting film 92 is formed using a circular vessel 91 like a petri dish. A height of a circular bottom portion 90 of the vessel 91 gradually decreases outward from a top 93 that is a center of the circular bottom portion 90. The bottom portion 90 has a conical shape similar to the surface 70 of the support 71 shown in FIGS. 8A and 8B. When a casting solution 63 is put in the vessel 91, a liquid level of the casting solution 63 becomes horizontal. Thus, the circular film 92 whose thickness increases outward from the center is formed.

Various changes and modifications are possible in the present invention and may be understood to be within the present invention.

What is claimed is:

1. A porous polymer film for culturing and screening cells comprising: a plurality of pores formed in a surface of said porous polymer film, the diameters of said pores gradually increasing as the distance of said pores increases from a predetermined point; wherein the thickness of the porous polymer film decreases as the size of the pores decreases such that the depth of each of said pores increases in proportion to a distance between said pores and said predetermined point or to a line orthogonal to a direction in which said diameters of said pores gradually increase from said predetermined point.

2. The porous film of claim 1, wherein said diameter of each of said pores increases in proportion to a distance between said predetermined point and said pores.

3. The porous film of claim 1, wherein said diameter of each of said pores increases in proportion to a distance between said pores and said line including said predetermined point.

* * * * *